United States Patent [19]

Morgan et al.

[11] Patent Number: 5,371,006
[45] Date of Patent: Dec. 6, 1994

[54] ISOLATED DNA ENCODING THE NOTI RESTRICTION ENDONUCLEASE AND RELATED METHODS FOR PRODUCING THE SAME

[75] Inventors: Richard D. Morgan, Middleton; Jack S. Benner, Hamilton, both of Mass.; Toby E. Claus, Portsmouth, N.H.

[73] Assignee: New England Biolabs, Inc., Beverly, Mass.

[21] Appl. No.: 3,254

[22] Filed: Jan. 11, 1993

[51] Int. Cl.$^5$ .................. C12N 9/22; C12N 15/55; C12N 15/70
[52] U.S. Cl. ................... 435/194; 435/320.1; 435/252.33; 435/193; 536/23.2
[58] Field of Search ............. 435/199, 193, 220.1, 435/252.33; 536/23.2

[56] References Cited

U.S. PATENT DOCUMENTS 5,202,248  4/1993  VanCott .

FOREIGN PATENT DOCUMENTS 0193413  9/1986  European Pat. Off. ...... C12N 15/00

OTHER PUBLICATIONS

Suggs, S. V., et. al. (1981) Proc. Natl. Acad. Sci., USA 78 (11) 6613–6617.
Saiki, R. K., et al. (1988) Science 239, 487–491.
Kosykh et al., Molec. Gen. Genet., 178:717–718 (1980).
Mann et al., Gene, 3:97–112 (1978).
Walder et al., Proc. Natl. Acad. Sci. USA, 78:1503–1507 (1981).
Bougueleret et al. Nucleic Acids Research, 12;3659–3676 (1984).
Gingeras & Brooks, Proc. Natl. Acad. Sci. USA, 80:402–406 (1983).
Theriault and Roy, Gene, 19:355–359 (1982).
Blumenthal et al., J. Bacteriol., 164:501–509 (1985).
Szomolanyi et al., Gene, 10:219–225 (1980).
Janulaitis et al., Gene, 20:197–204 (1982).
Kiss and Bauldauf, Gene, 21;111–119 (1983).
Walder et al., J. Biol. Chem., 258:1235–1241 (1983).
Raleigh and Wilson, Proc. Natl. Acad. Sci. USA, 83:9070–74 (1986).
Kiss et al., Nucleic Acid Research, 13:6403–6421 (1985).
Qiang and Schildkraut, Methods in Enzymology, 155:15–21 (1987).
Roberts, Nucleic Acid Research, Supp. 13:T165–r200.
Looney et al., Gene, 80:193–208 (1989).
Wilson, *Methods in Enzymology 216: Recombinant DNA Part G* ed. Wu, R., Academic Press, pp. 259–279 (1992).

Primary Examiner—Charles L. Patterson, Jr.
Attorney, Agent, or Firm—David G. Conlin; Gregory D. Williams; Peter F. Corless

[57] ABSTRACT

The present invention is directed to a method for cloning and producing the NotI restriction endonuclease by 1) introducing the restriction endonuclease gene from *Nocardia otitidis-caviarum* into a host whereby the restriction gene is expressed; 2) fermenting the host which contains the plasmid encoding and expressing the NotI restriction endonuclease activity, and 3) purifying the NotI restriction endonuclease from the fermented host which contains the plasmid encoding and expressing the NotI restriction endonuclease activity.

7 Claims, 4 Drawing Sheets

BamHI 14.5 kb fragment from *N. otitidis-caviarum*

Plasmid name: pRM189-1
Plasmid size: 7749 bp

Figure 4

DNA sequence of the 5' end of the NotI endonuclease gene

5' ATG CGG TCA GAT ACG TCG GTG GAG CCA GAG GGC GCC AAC TTC
ATC GCG GAA TTT TTC GGG CAT CGT GTG TAC CCC GAA GTC GTC AGC
ACT GAA 3'   SEQ ID:17

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 15 amino acids
( B ) TYPE: amino acid
( C ) STRANDEDNESS: unknown
( D ) TOPOLOGY: unknown ( x i ) SEQUENCE DESCRIPTION: SEQ ID NO:1:

```
Met Arg Ser Asp Thr Ser Val Glu Pro Glu Gly Ala Asn Phe Ile
1               5                   10                  15
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:2:

```
Met Arg Ser Asp Thr Ser Val Glu Pro Glu Gly Ala Asn Phe Ile Ala
1               5                   10                  15
Glu Phe Phe Gly Xaa Xaa Val Tyr Pro Glu Val
                20              25
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:3:

```
Ala Tyr Lys Phe Ala Leu Ser Gly Arg
1               5
```

( 2 ) INFORMATION FOR SEQ ID NO:4:

( i ) SEQUENCE CHARACTERISTICS:
        ( A ) LENGTH: 36 amino acids
        ( B ) TYPE: amino acid
        ( C ) STRANDEDNESS: unknown
        ( D ) TOPOLOGY: unknown ( i x ) FEATURE:
        ( A ) NAME/KEY:
        ( B ) LOCATION: 33
        ( D ) OTHER INFORMATION: /note ="Position 33, Xaa =Tyr or
            Arg"

( i x ) FEATURE:
        ( A ) NAME/KEY:
        ( B ) LOCATION: 36
        ( D ) OTHER INFORMATION: /note ="Position 36, Xaa =Lys or
            Leu"

( x i ) SEQUENCE DESCRIPTION: SEQ ID NO:4:

```
Asp Phe His Gly Ser Tyr Lys His Ala Val Gly Ala Ile Asp Ile Ala
1               5                   10                  15
Leu Val Glu Gly Ile Asp Phe His Gly Xaa Leu Pro Thr Pro Ala Gly
                20              25                  30
Xaa Ala Ala Xaa
        35
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:5:

GA NGC RAA YTT RTA NGC CAT        20

( 2 ) INFORMATION FOR SEQ ID NO:6:

( i ) SEQUENCE CHARACTERISTICS:
  ( A ) LENGTH: 20 base pairs
  ( B ) TYPE: nucleic acid
  ( C ) STRANDEDNESS: unknown
  ( D ) TOPOLOGY: unknown ( x i ) SEQUENCE DESCRIPTION: SEQ ID NO:6:

AA NGC RAA YTT RTA NGC CAT                    20

( 2 ) INFORMATION FOR SEQ ID NO:7:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:7:

GA SGC GAA CTT GTA SGC CAT                    20

( 2 ) INFORMATION FOR SEQ ID NO:8:

( i ) SEQUENCE CHARACTERISTICS:
    ( A ) LENGTH: 23 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:8:

GAR CCN GAR GGN GCN AAR TTY AT                23

( 2 ) INFORMATION FOR SEQ ID NO:9:

( i ) SEQUENCE CHARACTERISTICS:
    ( A ) LENGTH: 23 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:9:

GAG CCS GAG GGS GCS AAG TTC AT                23

( 2 ) INFORMATION FOR SEQ ID NO:10:

( i ) SEQUENCE CHARACTERISTICS:
    ( A ) LENGTH: 23 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:10:

AAR TTY ATH GCN GAR TTY TTY GG                23

( 2 ) INFORMATION FOR SEQ ID NO:11:

( i ) SEQUENCE CHARACTERISTICS:
    ( A ) LENGTH: 23 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:11:

AAG TTC ATC GCS GAG TTC TTC GG                23

( 2 ) INFORMATION FOR SEQ ID NO:12:

( i ) SEQUENCE CHARACTERISTICS:
    ( A ) LENGTH: 14 base pairs
    ( B ) TYPE: nucleic acid
    ( C ) STRANDEDNESS: unknown (D) TOPOLOGY: unknown (xi) SEQUENCE DESCRIPTION: SEQ ID NO:12:

GTN TAY CCN GAR GT                                    14

(2) INFORMATION FOR SEQ ID NO:13:

(i) SEQUENCE CHARACTERISTICS:
       (A) LENGTH: 12 amino acids
       (B) TYPE: amino acid
       (C) STRANDEDNESS: unknown
       (D) TOPOLOGY: unknown (xi) SEQUENCE DESCRIPTION: SEQ ID NO:13:

Ile Thr Ser Pro Pro Tyr Trp Gly Met Arg Thr Tyr
1               5                   10

(2) INFORMATION FOR SEQ ID NO:14:

(i) SEQUENCE CHARACTERISTICS:
       (A) LENGTH: 14 amino acids
       (B) TYPE: amino acid
       (C) STRANDEDNESS: unknown
       (D) TOPOLOGY: unknown (xi) SEQUENCE DESCRIPTION: SEQ ID NO:14:

Gly Gly Leu Val Leu Asp Pro Phe Ala Gly Thr Gly Arg Ala
1               5                   10

(2) INFORMATION FOR SEQ ID NO:15:

(i) SEQUENCE CHARACTERISTICS:
       (A) LENGTH: 37 base pairs
       (B) TYPE: nucleic acid
       (C) STRANDEDNESS: unknown
       (D) TOPOLOGY: unknown (xi) SEQUENCE DESCRIPTION: SEQ ID NO:15:

GACGCATATG CGTTCCGATA CGTCGGTGGA GCCAGAG               37

(2) INFORMATION FOR SEQ ID NO:16:

(i) SEQUENCE CHARACTERISTICS:
       (A) LENGTH: 24 base pairs
       (B) TYPE: nucleic acid
       (C) STRANDEDNESS: unknown
       (D) TOPOLOGY: unknown (xi) SEQUENCE DESCRIPTION: SEQ ID NO:16:

GAATGTCGAC CATCTCCACC CACG                            24

(2) INFORMATION FOR SEQ ID NO:17:

(i) SEQUENCE CHARACTERISTICS:
       (A) LENGTH: 93 base pairs
       (B) TYPE: nucleic acid
       (C) STRANDEDNESS: unknown
       (D) TOPOLOGY: unknown (xi) SEQUENCE DESCRIPTION: SEQ ID NO:17:

ATGCGGTCAG ATACGTCGGT GGAGCCAGAG GGCGCCAACT TCATCGCGGA

ATTTTTCGGG CATCGTGTGT ACCCCGAAGT CGTCAGCACT GAA        93

ISOLATED DNA ENCODING THE NOTI RESTRICTION ENDONUCLEASE AND RELATED METHODS FOR PRODUCING THE SAME

BACKGROUND OF THE INVENTION

The present invention relates to recombinant DNA which encodes the Not I restriction endonuclease and modification methylase, and the production of these enzymes from the recombinant DNA.

Restriction endonucleases are a class of enzymes that occur naturally in bacteria. When they are purified away from other contaminating bacterial component, restriction endonucleases can be used in the laboratory to cut DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. More than one hundred different restriction endonucleases have been identified among the many hundreds of bacterial species that have been examined to date.

Bacteria tend to possess only a small number of restriction endonucleases per species. The endonucleases typically are named according to the bacteria from which they are derived. Thus, the species *Neisseria lactamica* for example, synthesizes four different restriction endonucleases, named NlaI, NlaII, NlaIII and NlaIV. These enzymes recognize and cleave the sequences GGCC, GATC, CATG and GGNNCC respectively. *Escherichia coli* RY13, on the other hand, synthesizes only one enzyme, EcoRI, which recognizes the sequence GAATTC.

While not wishing to be bound by theory, it is thought that in nature restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of cleaving the DNA, they chemically modify one other of the nucleotides within the sequence by the addition of a methyl group. Following methylation, the recognition sequence is no longer bound or cleaved by the restriction endonuclease. The DNA of a bacterial cell is fully modified by virtue of the activity of its modification methylase, and is therefore insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins that they encode in greater quantities than are obtainable by conventional purification techniques. The standard approach to isolating clones of interest (restriction endonuclease genes) is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., Molec. Gen. Genet 178: 717–719, (1980); HhaII: Mann et al., Gene 3: 97–112, (1978); PstI: Walder et al., Proc. Nat. Acad. Sci. 78 1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acid. Res. 12: 3659–3676, (1984); PaeR7: Gingeras and Brooks, Proc. Natl. Acad. Sci. USA 80: 402–406, (1983); Theriault and Roy, Gene 19:355–359 (1982); PvuII: Blumenthal et al., J. Bacteriol. 164: 501–509, (1985)).

A third approach, which is being used to clone a growing number of systems, involves selection for an active methylase gene (See e.g., EPO No.: 193,413 published Sep. 3, 1986 and BsuRI: Kiss et al., Nucl. Acid. Res. 13: 6403–6421, (1985)). Since restriction and modification genes are often closely linked, both genes can often be cloned simultaneously. This selection does not always yield a complete restriction system however, but instead yields only the methylase gene (BspRI: Szomolanyi et al., Gene 10: 219–225, (1980); BcnI: Janulaitis et al, Gene 20: 197–204 (1982); BsuRI: Kiss and Baldauf, Gene 21: 111–119, (1983); and MspI: Walder et al., J. Biol. Chem. 258: 1235–1241, (1983)).

In some systems problems may arise in trying to introduce the endonuclease gene into a host not already protected by modification. If the methylase gene and endonuclease gene are introduced on a common DNA fragment, the methylase gene must modify or protect the host before the endonuclease gene cleaves the host's genome.

Another obstacle to cloning restriction-modification systems in *E. coli* was discovered in the process of cloning diverse methylases. Many *E. coli* strains (including those normally used in cloning) have systems that resist the introduction of DNA containing cytosine methylation. (Raleigh and Wilson, Proc. Natl. Acad. Sci., USA 83: 9070–9074, (1986)). Therefore, it is also necessary to carefully consider which E. coli strain(s) to use for cloning.

Another potential problem is that some restriction endonuclease and methylase genes may not express in E. coli due to differences in the transcription machinery of the source organism and E. coli, such as differences in promotors and ribosome binding sites. The methylase selection technique requires that the methylase express well enough in E. coli to fully protect at least some of the plasmids carrying the gene.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

The present invention relates to recombinant DNA encoding the genes for the NotI restriction endonuclease and modification methylase obtainable from *Nocardia otitidis-caviarum* (ATCC 14630) as well as related methods for the production of these enzymes from the recombinant DNA. The known methods for cloning restriction endonuclease genes were not successful in cloning NotI restriction endonuclease and modification methylase genes. Numerous attempts were made with the very successful method of selecting for an active methylase gene as well as the phage selection method. It is now known that these methods do not work because neither the methylase or endonuclease gene will be expressed when using the above methods. Therefore a novel approach was required in order to clone the NotI endonuclease and methylase genes. The new method involves purifying the NotI restriction endonuclease to homogeneity and determining the amino acid sequence of the N terminal end and of internal cyanogen-bromide degradation fragments of the protein. The amino acid sequence is used to make PCR primers to amplify a portion of the endonuclease directly from the *N. otitidis-caviarum* genome, which then serves as a probe to identify clones containing the entire gene.

This invention also relates to a transformed host which expresses the restriction endonuclease NotI, an enzyme which recognizes the DNA sequence 5'-GCGGCCGC-3' and cleaves in the recognition sequence between the first -CG- pair leaving a 4 base 5' overhang (Roberts, R., Nucl. Acid Res.,supplement 13:165 (1985)). NotI restriction endonuclease produced in accordance with the present invention is substantially pure and free of the contaminants normally found in restriction endonuclease preparations made by conventional techniques as described in step 2 of example 1. One preferred method for cloning the NotI restriction-modification system comprises: purifying the endonuclease from *N. otitidis-caviarum* to near homogeneity, determining the amino acid sequence of the N-terminus and internal cyanogen bromide fragments, making degenerate DNA primers based on the amino acid sequences, amplifying a portion of the endonuclease from genomic *N. otitidis-cariarum* DNA with the degenerate primers, selecting an appropriate vector, forming a library containing DNA from *N. otitidis-cariarum*, isolating those clones containing DNA which hybridizes to the amplified DNA corresponding to a portion of the endonuclease, sequencing the cloned DNA to determine the DNA sequence at the beginning of the endonuclease and to identify the adjacent methylase (the NotI methylase), amplifying the entire endonuclease by PCR and ligating it into an expression vector beginning at the NotI AUG start codon, pre-modifying an appropriate host cell with EagI methylase (-CGGCCG-) on a separate, compatible vector, introducing the above ligated expression vector containing the NotI endonuclease gene into the pre-modified host, growing the host and inducing with the appropriate expression conditions, harvesting the cells and purifying the NotI endonuclease.

BRIEF DESCRIPTION OF THE FIGURES

FIG. 4 is the DNA sequence of the 5' end of the NotI restriction endonuclease gene

DETAILED DESCRIPTION OF THE INVENTION

Figure 1:
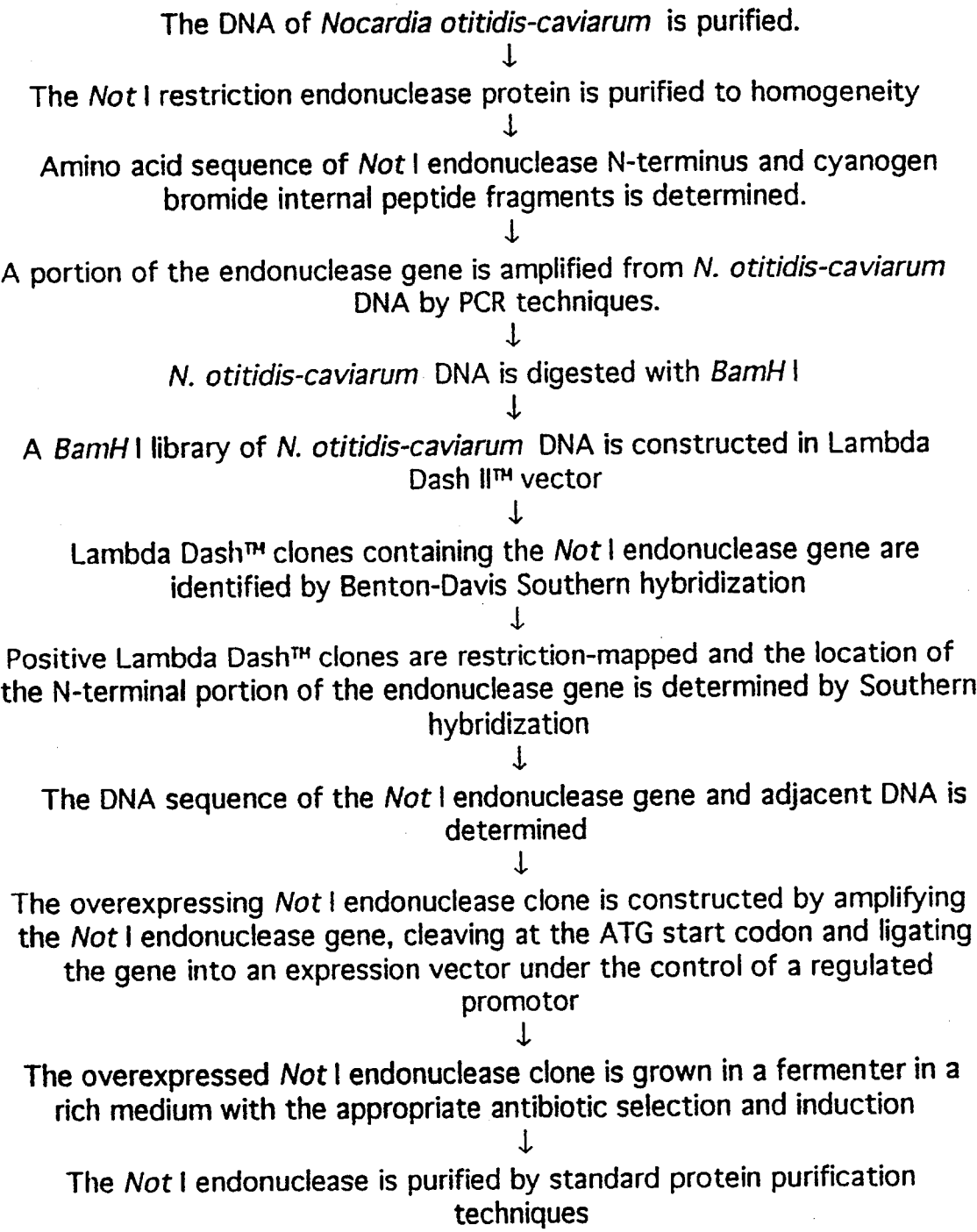
FIG. 1 illustrates the preferred method for cloning and producing the NotI restriction endonuclease. At the onset of the cloning project, it was not known which strategies or conditions would be successful in cloning the NotI restriction-modification system. Indeed, the methylase selection approach did not yield NotI methylase (nor endonuclease) clones. The protein sequencing, DNA amplification and the cloning results, and subsequent DNA sequencing, mapping, and characterization of the clones described in FIG. 1 and example 1 reveal the previously unknown direct pathway for cloning and expressing the NotI restriction-modification system.

The present invention relates to recombinant DNA which encodes the NotI restriction endonuclease, as well as to the enzyme produced from such a recombinant DNA.

The cloning of the NotI restriction endonuclease gene from *Nocardia otitidis-cariarum* proved to be unusually difficult. No methylase clones were obtained by the standard methylase selection procedure, even though many different libraries were constructed and screened. This appears to be due to a failure of the NotI methylase to express in E. coli at levels which would provide protection. The phage selection approach was also attempted without success. These results are consistent with the observed differences in transcription machinery between Nocardia and E. coli. Cloning the NotI endonuclease therefore required a novel approach.

The endonuclease protein was purified to near homogeneity and used to determine the amino acid sequence of portions of the protein. The N-terminal amino acid sequence was determined and the endonuclease was digested with cyanogen bromide, which produced 4 major peptide fragments of approximately 24 kD, 10 kD, 4 kD, and 3 kD in size. Unamibiguous amino acid sequence was determined for the 24 kD, 10 kD and 4 kD fragments, while the 3 kD peptide gave a mixed signal. The 24 kD peptide was found to be the N-terminal fragment of the endonuclease. Degenerate DNA primers based on the amino acid sequence of the N-terminal region and the 10 kD fragment were synthesized and used to amplify this portion of the endonuclease gene from genomic N. otitidis-caviarum DNA by PCR. The amplified DNA fragment of approximately 680 bp was subcloned into pUC19 and sequenced. The amino acid sequence deduced from the DNA sequence of this PCR fragment matched the amino acid sequence of the NotI endonuclease determined from the N-terminal (24 kD), 10 kD and 4 kD peptides, confirming that this DNA fragment represented a portion of the NotI endonuclease gene. A library of N. otitidis-caviarum DNA was constructed in a Lambda Dash vector system to generate clones containing 9 to 23 kb inserts of N. otitidis-caviarum DNA. The 680 bp fragment of the endonuclease gene was used as a probe to identify Lambda Dash clones containing this portion of the endonuclease gene. These lambda clones were purified and all were found to contain a 14.5 kb BamHI fragment. The location of the probe was mapped onto the BamHI fragment to approximately position 8200 to 8900. This result indicated the entire endonuclease gene was probably present, since the clones contained approximately 8200 bp to one side of the probe and approximately 5600 bp to the other side. The 14.5 kb BamHI fragment was subcloned into pUC19 and assayed for NotI endonuclease and methylase, but neither activity was detected. This result suggests that the endonuclease and methylase genes are not expressed in E. coli when the original Nocardia DNA upstream of the genes remains in place. The DNA flanking the probe was sequenced and the exact nucleotide sequence at the N-terminal of the endonuclease gene was determined. DNA primers were designed to amplify the entire NotI endonuclease gene, from the N-terminal end of the NotI gene, introducing an NdeI site at the ATG start codon (-CATATG-), to a SalI site approximately 500 bp 3-prime of the end of the NotI gene. The entire gene was amplified, both from the 14.5 kb BamHI plasmid and from the genomic N. otitidis-cariarum DNAs. The amplified DNA was cleaved by NdeI and SalI endonucleases and ligated into the T7 expression vector pSYX22, which had been previously cleaved by SalI and NdeI. The ligation reaction was transformed into ER2169 competent cells premodified with the EagI methylase (-CGGCCG-) on the compatible plasmid pACYC184. Vectors containing inserts of the desired size were identified by miniprep procedures. These clones were grown to mid-log phase and induced with IPTG. The cells were then harvested by centrifugation, resuspended in sonication buffer and lysed by sonication. The extract was clarified and assayed for NotI endonuclease activity. Clones derived from N. otitidis-caviarum genomic DNA and from the 14.5 kb BamHI fragment plasmid produced NotI activity at 5,000,000 units per gram of cells (wet weight).

The method described herein by which the NotI restriction gene is preferably cloned and expressed is illustrated in FIGS. 1 and includes the following steps:

1. The DNA of *Nocardia otitidis-caviarum* is purified.
2. The NotI restriction endonuclease protein is purified to homogeneity by standard protein purification techniques.
3. The N-terminal amino acid sequence of the purified NotI endonuclease is determined. The purified NotI endonuclease is cyanogen bromide digested to produce internal peptide fragments, and amino acid sequence is determined from these fragments.
4. Degenerate DNA primers are synthesized based on the amino acid sequence of the N-terminus and an internal peptide fragment. These primers are used to amplify a portion of the endonuclease gene from N. otitidis-caviarum DNA by PCR techniques.
5. The N. otitidis-cariarum DNA is digested completely and/or partially with a restriction endonuclease such as BamHI, or any of its isoschizomers, that cleaves to produce a fragment(s), clonable in Lambda Dash II or any similar vector, which contains the entire NotI endonuclease gene.
6. The digested DNA's are ligated to the lambda phage cloning vector. The resulting mixtures are packaged in vitro and used to infect an appropriate host, such as E. coli strain ER1458 (available from New England Biolabs, Inc., Beverly, Mass.). The titer of infective phage is determined by plating a portion of the packaged phage and counting the resultant plaques.
7. The in vitro packaged phage are preferably plated at varying densities in a soft agar lawn of an appropriate E. coli host, such as ER1458 on rich media. After incubation, phage containing the NotI endonuclease gene are identified by Benton-Davis Southern hybridization, using the PCR derived portion of the NotI endonuclease as probe against nitrocellulose filter lifts of the plaques. Positive plaques are removed from the plates and purified by several successive rounds of plating and hybridization.
8. In order to determine the location of the NotI endonuclease gene on the above clones, and thus whether the clones contain enough DNA to encode the entire endonuclease gene, and also any adjacent methylase gene, the cloned fragment is restriction-mapped and the location of the N-terminal portion of the endonuclease gene is determined by Southern hybridization to various restriction digests of the clones using the same probe as above. If there is enough DNA to encode the entire restriction gene, proceed to step 9. If there is not enough DNA on the 3' side of the probe to encode the complete restriction gene, more clones are screened and/or a different library of clones made.

The N. otitidis-caviarum DNA inserts in the lambda Dash vectors may be subcloned into a plasmid vector, such as pUC19 (ATCC# 37254), in order to simplify mapping and genetic manipulation of the insert, and to determine if the clones produce either NotI endonuclease or methylase. In the present invention, clones of the 14.5 kb BamHI fragment in either orientation in pUC19 did not produce detectable levels of NotI endonuclease in vitro. The fragment also contained 4 NotI sites which were all completely cleaved in vitro by NotI, indicating that there was no in vivo NotI methylase activity.

9. The DNA including and adjacent to the N-terminus to internal 10 kD cyanogen-bromide fragment probe is sequenced to determine the gene orientation, the exact DNA sequence at the N-terminus of the gene, and to check for the presence of a cytosine methylase gene adjacent to the NotI endonuclease gene.
10. Overexpressing the NotI endonuclease gene: There are a number of ways in which the clone containing the restriction gene can be overexpressed. The DNA sequence and detailed mapping help determine the best approach for overexpression of the restriction endonuclease gene. One approach for overexpression comprises designing primers that hybridize directly at the N-terminus of the restriction endonuclease gene and somewhere downstream of the restriction endonuclease gene in order to use the polymerase-chain reaction to amplify the entire restriction endonuclease gene. The resulting DNA fragment can be cleaved to remove all Nocardia DNA preceding the endonuclease gene and can be inserted into an expression vector such as pSYX22 directly downstream of an inducible promoter such as T7. Alternatively, overexpression can be accomplished by inserting a promoter recognized strongly by *E. coli*, such as $P_{tac}$ on pAGR3 (available from New England Biolabs) directly in front of the beginning of the restriction endonuclease gene. This may be accomplished by finding convenient restriction sites near the beginning and end of the restriction endonuclease gene and compatible restriction sites near the promoter of pAGR3, and transferring the restriction gene into pAGR3 in line with the $P_{tac}$ promoter. Other regulated promoters which can be used are PlacUV5 (Fuller, Gene 19:43–54, (1982)), and λPL (Shimatake and Rosenberg, Nature 254:128, (1981)) on pUC19 and pBR322 derivatives. In addition, a strong ribosome binding site (Shine & Dalgarno, Proc. Natl. Acad. Sci. USA 71, 1342–1346, (1974)) can be placed in front of the gene to increase expression.

11. In accordance with the present invention, to obtain a stable clone which overexpresses the restriction endonuclease, the host is pre-protected from restriction endonuclease digestion. This is accomplished by cloning in either the NotI methylase, or a heterologous methylase such as EagI which protects from NotI digestion by modifying sites which overlap NotI restriction sites, on a separate plasmid. The plasmid used must be compatible with the expression vector. The methylase must also be produced at a level which will protect the host's genome from digestion by the overexpressed restriction endonuclease gene. In the present invention it was found that the EagI methylase gene cloned on a low copy number plasmid, such as pACYC184 (Chang and Cohen, J. Bacteriol., 134:1131 (1978)), gave adequate protection of the host genome from NotI digestion.

The DNA sequence of the gene can be altered by site-directed mutagenesis or by resynthesizing the gene itself to use codons that are more efficiently utilized in *E. coli* (Ikemura, J. Mol. Biol. 151:389–409, (1981)). In the present invention the second and third codons of the endonuclease gene were changed to the codons most frequently used by *E. coli* through the PCR amplification process.

12. Production: The NotI endonuclease may be produced from clones carrying the EagI methylase gene (or the NotI methylase gene) and the overexpressed NotI restriction endonuclease gene by propagation in a fermenter in a rich medium with the appropriate antibiotic selection and induction. The cells are thereafter harvested by centrifugation and disrupted by sonication to produce a crude cell extract containing NotI restriction endonuclease activity.

13. Purification: The crude cell extract containing the NotI endonuclease is purified by standard protein purification techniques such as affinity-chromatography, or ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE 1

Cloning of Not I Modification Methylase and Restriction Endonuclease Genes

1. DNA purification: To prepare the DNA of *Nocardia otitidis-caviarum*, 6 g of cell paste was resuspended by shaking gently for 10 min in 20 ml of 25% sucrose, 0.05M Tris-HCl, 1 mM EDTA pH 8.0. 10 ml of 0.25M EDTA pH 8.0 and 6 ml of freshly prepared 10 mg/ml lysozyme in 0.25M Tris-HCl pH 8.0 was added and the solution was incubated at 4° C. for 16 hours. The suspension was then quick frozen in liquid nitrogen and then thawed in a 37° C. water bath three times. Proteinase K was added to a final concentration of 1 mg/ml and incubated 16 hours at 50° C. The solution was extracted with 50 ml of equilibrated phenol, the aqueous phase was recovered and extracted with 50 ml of chloroform two times. The DNA was precipitated by the addition of 1/10th volume 3M NaAcetate pH 6.0 and 1 volume of 2-propanol and collected by centrifugation. The DNA pellet was air dried for 1 hour, then resuspended in 3 ml of DNA buffer (10 mM Tris-HCl, 1 mM EDTA pH 8.0) containing 100 μg/ml RNase and incubated at 37° C. for 1 hour. 5M NaCl was then added to a final concentration of 0.4M and the DNA precipitated by the addition of 1 volume of 2-propanol. The DNA precipitate was hooked out of the solution on a glass rod, air dried and dissolved in 1.5 ml DNA buffer to a final concentration of approximately 200 μg/ml.

2. Purification of the NotI restriction endonuclease from *Nocardia otitidis-cariarum*: NotI restriction enzyme may be produced from *Nocardia otitidis-caviarum* by propagation to mid-log phase in a fermentor containing rich broth. The cells are harvested by centrifugation. All of the following procedures were performed on ice or at 4° C. 384 g of cells were resuspended in 770 ml of buffer A (10 mM $KPO_4$, pH 6.8, 0.1M NaCl, 0.1 mM EDTA, 5% glycerol) and broken by passing 5 times through a Gaulon Homogenizer at 11,500 PSIG. The extract was centrifuged at 12,000 rpm for 40 minutes at 4° C. The supernatant was loaded onto a phosphocellulose column (5×12 cm) equilibrated with buffer A. The column was washed with 200 ml buffer A, followed by a linear gradient of NaCl formed with 1100 ml buffer A and 1100 ml buffer A plus NaCl added to 1.5 M. 25 ml fractions were collected. The peak of restriction enzyme activity eluted from the column between 0.4 and 0.6M NaCl and was pooled. The P-cell pool was dialyzed against buffer B (0.1M NaCl, 10 mM Tris-HCl pH 7.5, 10 mM $MgCl_2$, 50 mM $NH_4SO_4$, 5% glycerol and 0.15% NaAzide) overnight. The pool was then loaded onto a Baker-bond Wide-pore PEI (NH) ® column (1.5×16 cm) equilibrated with buffer B. The column was washed with 30 ml buffer B and then a 400 ml linear gradient of buffer B, 0.1M NaCl to 1.6M NaCl was applied. The peak of restriction enzyme activity eluted at 0.6 to 0.8M NaCl and was pooled. The PEI pool was dialyzed overnight against buffer C (10 mM Tris-HCl pH 7.5, 0.1 mM EDTA, 50 mM NaCl, 5% glycerol) and then loaded onto a Mono-Q® column (Pharmacia), equilibrated with buffer C. A 40 ml linear gradient of 0.1M NaCl to 0.6 M NaCl was applied. The restriction enzyme activity eluted at 0.3M NaCl and was pooled. The Mono-Q® pool was diluted with 3 X volume of buffer D (20 mM KPO$_4$, pH 6.8, 0.1 mM EDTA, 5% glycerol) and loaded onto a Mono-S® column (Pharmacia) at 50 mM NaCl A 40 ml linear gradient in buffer D from 50 mM NaCl to 0.5M NaCl was applied. The restriction enzyme activity eluted at 0.25M NaCl and was pooled. A second Mono-Q® column was run as previously described to insure the homogeneity of the endonuclease protein. The final NotI restriction endonuclease preparation gave one major band of approximately 42 kD on a 10–20% SDS-PAGE gel stained with Coomassie blue R-250.

3. The NotI restriction endonuclease, prepared as described in section 2 above, was subjected to electrophoresis and electroblotted according to the procedure of Matsudaira (Matsudaira, P., J. Biol. Chem. 262:10035–10038, 1987), with modifications as previously described (Looney, M. C., Moran, L. S., Jack, W. E., Feehery, G. R., Benner, J. S., Slatko, B. E., & Wilson G. G., Gene 80:193–208, 1989). The membrane was stained with Coomassie blue R-250 and the protein band of approximately 42 kd was excised and subjected to sequential degradation (Waite-Rees, P. A., Keating, C. J., Moran, L. S., Slatko, B. E., Hornstra, L. J. and Benner, J. S., J. Bacteriol. 173:5207–5219, 1991).

The first 15 residues of the 42 kd protein corresponded to Met-Arg-Ser-Asp-Thr-Ser-Val-Glu-Pro-Glu-Gly-Ala-Asn-Phe-Ile, SEQ ID:1. An additional sample of the NotI endonuclease, 20 μg in 20 μl, was treated with 2 mg of cyanogen bromide (Sigma) dissolved in 200 μl of 88% distilled formic acid for 24 hours in the dark at room temperature. This reaction mixture was evaporated to dryness and resuspended in 20 μl of loading buffer (1.5M Tris-HCl, pH 8.5, 12% glycerol, 4% SDS, 0.05% Serva Blue G, 0.05% Phenol Red) at 100° C. for 5 minutes. This sample was subjected to electrophoresis on a Tris-Tricine 10 to 20% polyacrylamide gradient gel (Novex) for three hours and then transferred to a polyvinylidene difluoride (PVDF) membrane (Problott, Applied Biosystems Inc.) using 10 mM CAPS buffer (10 mM 3-[cyclohexylamino]-1-propanesulfonic acid, 10 % methanol, 0.05% SDS, 0.005% dithiotheritiol, adjusted to pH 11.0 with NaOH) for 18 hours at 200 volts in a tank electroblotter (TE52, Hoeffer). The membrane was stained with Coomassie blue R-250 and major bands of 24 kd, 10 kd, 4 kd and 3 kd were observed. These stained protein bands were excised from the membrane and each subjected to sequential degradation (2). The first 27 residues of the 24 kd peptide corresponded to Met-Arg-Ser-Asp-Thr-Ser-Val-Glu-Pro-Glu-Gly-Ala-Asn-Phe-Ile-Ala-Glu-Phe-Phe-Gly-X-X-Val-Tyr-Pro-Glu-Val, SEQ ID:2. Residues 21 and 22 were not identified. This fragment was therefore determined to be derived from the N-terminus of the endonuclease. All other fragments are derived from internal cleavage by cyanogen bromide at Met residues from within the protein and thus should be preceded by a Met. The first 9 residues of the 10 kd peptide corresponded to Ala-Tyr-Lys-Phe-Ala-Leu-Ser-Gly-Arg, SEQ ID:3. The first 36 residues of the 4 kd peptide corresponded to Asp-Phe-His-Gly-Ser-Tyr-Lys-His-Ala-Val-Gly-Ala-Ile-Asp-Ile-Ala-Leu-Val-Glu-Gly-Ile-Asp-Phe-His-Gly-X-Leu-Pro-Thr-Pro-Ala-Gly-(Tyr or Arg)-Ala-Ala-(Lys or Leu), SEQ ID:4, where residue 26 was undetermined and residues 33 and 36 were somewhat ambiguous. The 3 kd peptide band produced two signals in most cycles and appeared to be a mixture of two peptides.

4. The peptide sequence data from intact NotI endonuclease, the 24 kd and 10 kd peptides and their known orientations were used to construct a series of eight PCR primers:

1) GA NGC RAA YTT RTA NGC CAT 20-mer, SEQ ID 5
2) AA NGC RAA YTT RTA NGC CAT 20-mer, SEQ ID:6
3) GA SGC GAA CTT GTA SGC CAT 20-mer, SEQ ID:7
4) GAR CCN GAR GGN GCN AAR TTY AT 23-mer, SEQ ID:8
5) GAG CCS GAG GGS GCS AAG TTC AT 23-mer, SEQ ID:9
6) AAR TTY ATH GCN GAR TTY TTY GG 23-mer, SEQ ID:10
7) AAG TTC ATC GCS GAG TTC TTC GG 23-mer, SEQ ID:11
8) GTN TAY CCN GAR GT 14-mer, SEQ ID:12 where
Y=T,C
R=A,G
H=A,T,C
S=G,C
N=A,C,G,T

Primers 1 through 3 are derived from the NotI 10 kd CNBr peptide and were prepared to prime toward the 5′ end of the gene. Primers 4 through 8 are derived from the NotI 24 kd CNBr peptide and were prepared to prime toward the 3′ end of the gene. Primers 3, 5 and 7 do not contain any A or T residues at the wobble positions.

5. Primers 3, 5, 7 and 8 were used to amplify the portion of the endonuclease gene between the N-terminus region (primers 5, 7 and 8) and the amino-end of the 10 kD cyanogen-bromide fragment (primer 3). Three different Mg++ concentrations and four different annealing temperatures were tried. A master reaction mix was made containing 65 μl 10 X Vent ™ reaction buffer, 7μl of 10 mg/ml BSA, 40μl of 4 mM dNTP solution, 33 μl DMSO, 3.5μl (700 ng) *Nocardia otitidiscaviarum* DNA, 408μl dH$_2$O, 13μl (650 ng) primer 3, 13μl (650 ng) primer 5 and 20μl (40 u) Vent exo- ™ polymerase. The mix was split into three 200μl aliquots; to the first was added 16μl dH$_2$O (final concentration Mg++=2 mM), to the second was added 6μl 100 mM MgSO$_4$ and 10μl dH$_2$O ([Mg++]=5 mM) and to the third was added 16μl 100 mM MgSO$_4$ ([Mg++]=10 mM). These reaction mixtures were divided into fourths and amplified using four different annealing temperatures. The reactions using primer 3 with primer 7 and the reactions using primer 3 with primer 8 were performed in the same way. The PCR amplification conditions were 95° C. for 1 minute, 45° C. (or 50° C., 55° C., 60° C.) for 1 minute and 72° C. for 1.5 minutes, for 35 cycles. 15μl of the PCR reaction product was analyzed by electrophoresis on a 1% agarose gel. A band of the desired size was observed in all of the primer 3 to primer 5 reactions except the 2 mM Mg++/60° anneal reaction. The primer 3 and primer 7 reactions yielded a band of the desired size in all three reactions annealed at 45° C. and in the 5 mM and 10 mM Mg++ reactions at 50° C. and 55° C. annealing, but not in the reactions at other conditions. The combination of primer 3 and primer 8 yielded a band of the desired size in only the 45° C. anneal 5 mM and 10 mM Mg++ and the 50° C. anneal, 10 mM Mg++ reactions. The bands of the desired size were electrophoresed into 1% LMP agarose, excised from the gel, melted at 65° C. for five minutes, cooled to 40° C. for 5 minutes and the agarose was digested by the addition of 1μl (1 u) β-agarase (New England Biolabs, Inc. Beverly, Mass.) with incubation at 40° C. for 1 hour.

6. Partial digestion: The purified DNA was cleaved with BamHI to achieve partial digestion as follows: 500μl of *Nocardia otitidis-caviarum* DNA at 50μg/ml in NEBuffer BamHI (150 mM NaCl, 50 mM Tris-HCl 10 mM MgCl$_2$, 1 mM DTT, pH 7.9 @ 25° C.) was divided into one 100μl aliquot and seven, 50μl aliquots. To the 100μl tube was added 20 units of BamHI to achieve 4 unit of enzyme per μg of DNA. 50μl was withdrawn from the first tube and transferred to the second tube to achieve 2 units BamHI/μg, and so on, each succeeding tube receiving half of the previous amount of BamHI. The tubes were incubated at 37° C. for one hour, then phenol/chloroform extracted, precipitated with 2 volumes ethanol, dried and resuspended in 20μl TE (TE=10 mM Tris-HCl, mM EDTA, pH 8.0) and 3μl from each was analyzed by agarose gel electrophoresis. Tubes exhibiting limit digestion and moderate, but incomplete digestion were chosen as the source of fragments for cloning. The separate reactions were mixed together and used as described in step 7 below.

7. BamHI library: A BamHI genomic library was constructed using the vector Lambda Dash™ II (Stratagene). Lambda Dash™ II is a lambda substitution vector that can be used to clone DNA fragments of 9-23 kb. 250 ng (2μl) of BamHI complete and partially digested *Nocardia otitidis-caviarum* DNA, as described above, was mixed with 500 ng of BamHI-cleaved lambda Dash™ II arms (0.5μl). 2.5μl of 2 X ligation mix (100 mM Tris pH 7.8, 20 mM MgCl$_2$, 20 mM DTT, 2 mM ATP) containing 1×10$^3$ units T4 DNA ligase was added and the mixture incubated at 17° C. for 16 hours. 2.5μl of the ligation reaction was packaged in vitro into infective phage particles using Gigapack® II Plus (Stratagene) according to the manufacturers instructions. Following incubation at room temperature for two hours, the packaged phage were diluted in 500μl of SM (SM=100 mM NaCl, 8 mM MgSO$_4$, 50 mM Tris-HCl pH 7.5, 0.01% gelatin) plus three drops of chloroform. The titer of infective phage particles was determined as follows. 2μl of the packaged phage solution was diluted into 198μl SM. 1μl, 10μl and 100μl aliquots of the diluted phage was added to 100μl of a fresh suspension of ER1458 cells (in 10 mM Tris-HCl pH 7.5, 10 mM MgCl$_2$, O.D.$_{600}$=2.0), incubated at RT for 15 minutes, then mixed with 3 ml top agar at 40° C. and spread on rich plates. After the top agar hardened the plates were incubated at 37° C. overnight. The plaques were counted the next day and the titer of the phage stock used in subsequent experiments was calculated to be 2.8×10$^5$ pfu/ml.

8. The in vitro packaged phage were plated, as above, to form well separated plaques in lawns of *E. coli* ER1458. Plates of approximately 600, 1500, 3000 and 5000 phage were made. Nitrocellulose filter plaque lifts of these clones from the lambda Dash™ BamHI library were probed with radio-labeled (Random Priming System I, New England Biolabs, Inc. Beverly, Mass.), gel purified PCR product from the primer 3 to primer 5 amplification reaction (above) (Benton-Davis method, In: *Molecular Cloning, a Laboratory Manual* by T. Maniatis, E. F. Fritsch and J. Sambrook, Cold Spring Harbor Laboratory Press, 1982, pp 320ff). 17 positive plaques were identified and all were plaque purified. DNA was prepared from confluent plate lysates (in top agarose) of 6 phage and digested with BamHI. All six contained a common 14.5 kb BamHI fragment, to which the primer 3 to primer 5 probe hybridized.

Figure 2:
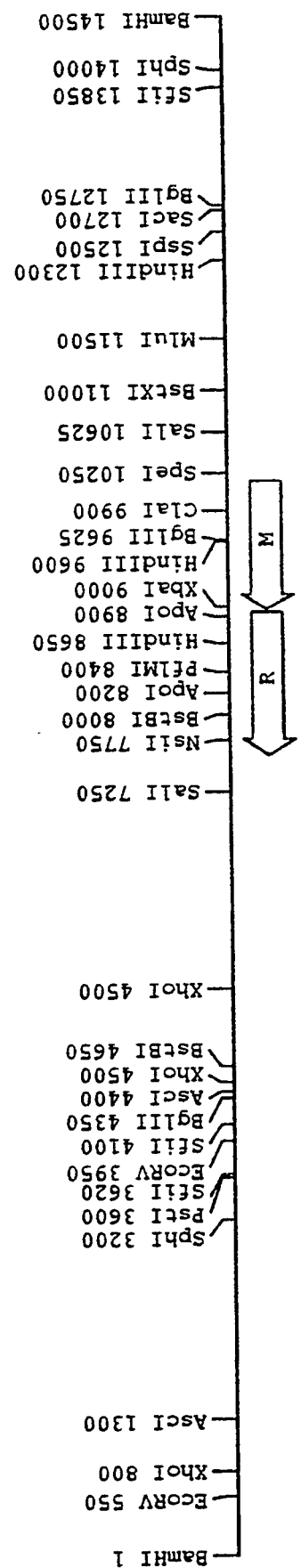
FIG. 2 is a restriction map of the 14.5 kb BamHI fragment of *N. otitidis-cariarum* DNA obtained from hybridization of the amplified portion of the NotI endonuclease gene to the BamHI Lambda Dash II library. The location and orientation of the NotI endonuclease and methylase genes are indicated.
Figure 3:
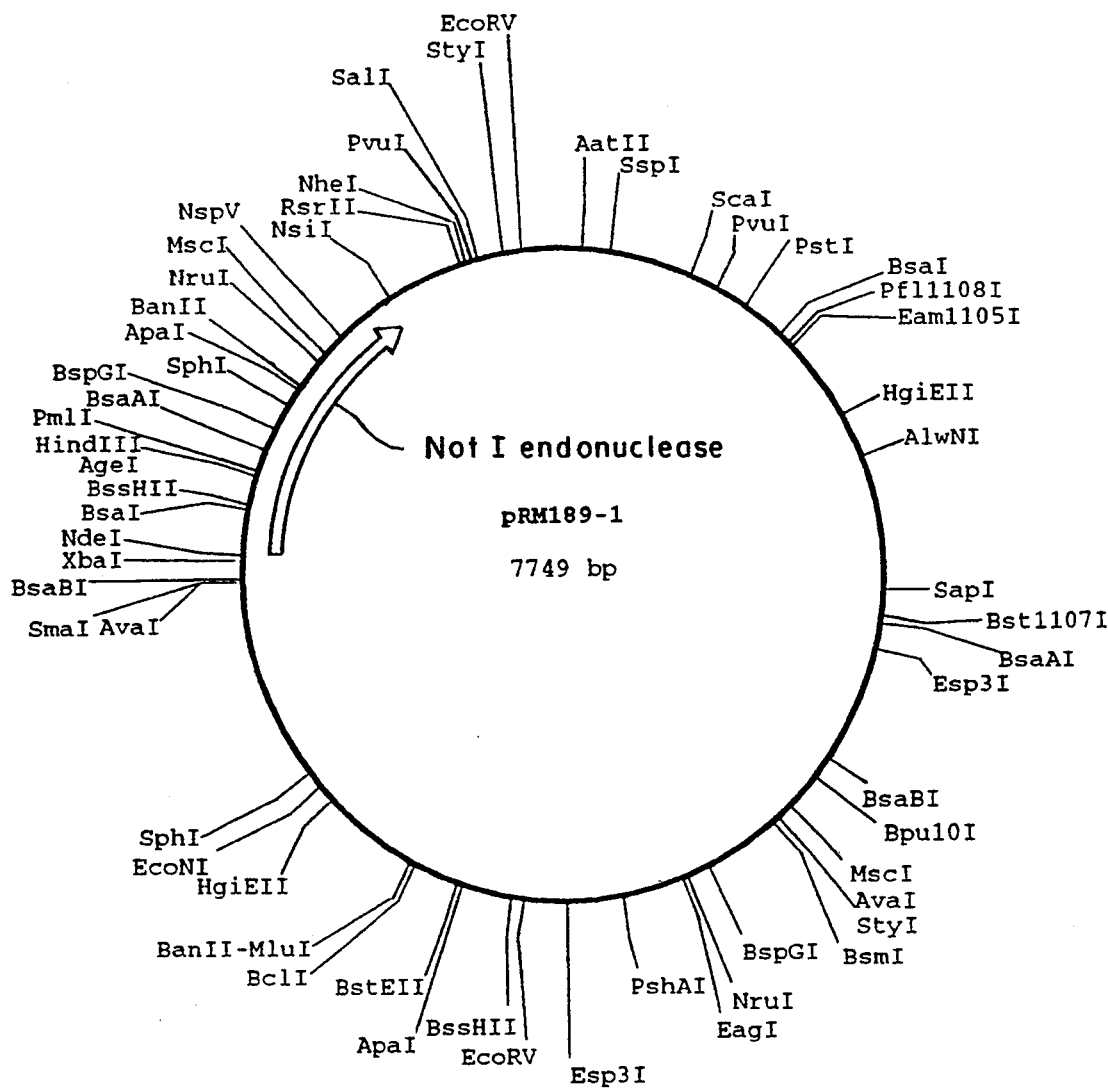
FIG. 3 is a restriction map of the over-expression clone pRM189-1.

9. Mapping the 14.5 kb BamHI fragment: The 14.5 kb BamHI fragment of *Nocardia otitidis-caviarum* DNA identified in lambda Dash™ II clones was subcloned into pUC19 for ease of mapping, creating clone pNOTB14.5. The pNOTB14.5 clone was digested with various restriction endonucleases according to the manufacturers instructions and a restriction map of the fragment determined (FIG. 2). The location of the NotI endonuclease gene on this clone was determined by Southern hybridization (Southern, E. 1975, J.Mol.Bio., 98:503) of the primer 3 to primer 5 probe (above) to restriction digests of the clone, of which the HindIII, PflMI, XbaI, ClaI and BstBI digests were particularly useful in locating the probe on the 14.5 kb BamHI fragment (FIG. 2). The probe hybridized near the middle of the BamHI fragment, with approximately 8200 bp to one side and 5600 to the other, indicating that there was ample DNA present to contain the entire restriction and modification genes. The pNOTB14.5 clone was grown and assayed for NotI restriction activity, but none was detected. No in vivo methylase activity was detected as assessed by the ability of NotI enzyme to completely cleave 4 sites in the cloned DNA.

In order to facilitate sequencing of the region of the clone near the probe, various subclones of pNOTB14.5 were constructed. Subclones were made by deleting portions of the clone, or by cleaving with a restriction enzyme(s), gel prepping the desired fragment and ligating it into an appropriately cleaved and dephosphorylated pUC19 vector. Clones of the desired construct were identified by performing minipreps, digesting the purified DNA and analyzing it by agarose gel electrophoresis.

Analysis of plasmid clones: Individual transformants were innoculated into 10 ml cultures of L-broth containing ampicillin and the plasmids that they carried were prepared by the following miniprep plasmid purification procedure, adapted from the method of Birnboin and Doly (Nucleic Acids Res. 7:1513, 1979).

Miniprep Procedure: Each culture was centrifuged at 8000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells and then placed on ice. Once the solutions had cleared, 1.5 ml of 3M sodium acetate pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were dissolved in 500µl of 10 mM Tris pH 8.0, 1 mM EDTA, containing 50 µg/ml RNase and incubated for 1 hour at 37° C. to digest the RNA. The DNA was precipitated by the addition of 50µl of 5M NaCl followed by 350µl of isopropanol. After 10 minutes at room temperature, the DNA was spun down by centrifugation for 5 minutes, the supernatants were discarded, the pellets were dried and then redissolved in a final solution of 150µl of 10 mM Tris, 1 mM EDTA pH 8.0. The plasmid minipreps were subsequently analyzed by digestion with various restriction endonucleases.

10. DNA Sequencing: DNA sequencing was performed using the Circumvent ™ DNA sequencing kit (New England Biolabs) according to the manufacturers instructions. Miniprep DNA preparations were used as templates. The DNA sequence provided data to use as a basis for subsequent manipulations to clone the entire restriction endonuclease gene and to induce expression of the cloned gene in E. coli. The amino acid sequence deduced from the DNA sequence matched the protein sequence of the N-terminus (24 kD peptide), the 10 kD, the 4 kD and by deduction two small (around 3 kD) peptides, and demonstrated the order of the peptides fragments to be 24 kD, 4 kD, 3(A) kD, 10 kD, 3(B) kD. The exact DNA sequence at the N-terminus of the protein was used to design a PCR amplification primer for expression of the NotI gene. Sequence around a SalI site occurring downstream of the endonuclease gene was used to design the second PCR expression primer. The sequence upstream of the endonuclease gene did not contain typical E. coli transcription factors, which is consistent with the lack of expression from pNOTB14.5. Concensus motifs for a β-type N4-methyl cytosine methylase gene, motif IV=Ile-Thr-Ser-Pro-Pro-Tyr-Trp-Gly-Met-Arg-Thr-Tyr, SEQ ID:13, and motif I=Gly-Gly-Leu-Val-Leu-Asp-Pro-Phe-Ala-Gly-Thr-Gly-Arg-Ala, SEQ ID:14 (Wilson,, G. G., In:*Methods in Enzymology*, 216:*Recombinant DNA Part G* ed Wu, R., Academic Press, 1992, pp 259–279), were found in a reading frame preceding and in the same orientation as the NotI endonuclease gene, separated from the start of the endonuclease by 44 nt. This data is consistent with a linked R-M system.

11. Overexpression of NotI restriction endonuclease: The restriction endonuclease gene was overexpressed by inserting the gene into an expression vector, pSYX22, directly downstream of an inducible promotor (T7) and strongly recognized ribosome binding site. To accomplish this, two oligonucleotide primers were made using the DNA and protein sequence data. The first oligonucleotide primer contained the sequence which overlaps the ATG codon, indicated by protein sequencing to be the start of the endonuclease gene, with three bases changed to create an NdeI site, and the third-position base of the second and third codons of the endonuclease changed to the preferred E. coli codon usage: 5' GACG CAT ATG CGT TCC GAT ACG TCG GTG GAG CCA GAG 3' SEQ ID NO:15 (NdeI site underlined, nucleotides changed from N. otitidis-caviarum sequence in bold). The second oligonucleotide primer contains sequence approximately 500 nucleotides 3' to the end of the NotI endonuclease gene, with a SalI site, present in the N. otitidis-caviarum DNA, included in the primer to aid the cloning of the fragment once amplified: 5' GAAT GTC GAC CAT CTC CAC CCA CG 3' SEQ ID NO:16 (SalI site underlined). These two primers were used with genomic N. otitidis-caviarum DNA and the pNOTB14.5 plasmid as the template in PCR reactions using Vent ™ DNA polymerase (95° C. - 1 min, 56° C. - 1 min, 72° C. - 2 min; 10 cycles from pNOTB14.5 and 20 cycles from the genomic DNA) to amplify a 1.7 kb DNA fragment containing the NotI endonuclease gene. The band was gel purified as described in Step 5. The purified PCR product was digested with 20 U of NdeI and 20 U SalI in 1X NEBuffer 3 for 1 hr. After incubation the digest was extracted once with a 1:1 mixture of phenol:chloroform, once with chloroform, and precipitated with 2 volumes of ethanol. The DNA was pelleted by centrifugation, washed once in 70% ethanol, dried and resuspended in 20µl TE. 3µl of the purified fragment (~0.1 µg) was ligated into the T7 expression vector, pSYX22 (from S. Xu, New England Biolabs), which had been digested with NdeI and SalI (~0.05 µg) in a total volume of 20µl with 400 U of T4 DNA ligase at 17° C. for 4 hours. [Derivation of pSYX22: pET-11a is a T7 expression vector derived from pBR322 that contains a lac operator 4 bp down stream of the T7 promoter (This T7 promoter plus lac operator is called T7llac promoter), the lacI$^q$ gene, and two restriction sites, NdeI and BamHI, for cloning (Dubendorff, J. W. and Studier, F. W., J. Mol. Biol. 219: 45–59, 1991). A pET-11a derivative, pAII17, was constructed that contains four copies of rrnB transcription terminator (pAII17 constructed by William Jack at New England Biolabs, Beverly, Mass.) upstream of the T7 promoter. The transcription terminator upstream of T7 promoter further decreases basal level of expression of the target gene. For convenience of cloning, the BamHI site on the vector was filled-in with klenow fragment of E. coli DNA polymerase I and a SalI linker was inserted to replace the BamHI site. This plasmid was named pSYX22.]. 10µl of the ligation was used to transform competent E. coli ER2169 (available from New England Biolabs, Inc., Beverly, Mass.) pre-modified with the EagI methylase gene on pEagM184-A [The EagI methylation recognition site, CGGCCG, overlaps the NotI restriction endonuclease recognition site and so protects the host from NotI digestion. pEagM184-A is derived from pA-CYC184, a low copy number plasmid that carries cam$^r$ and Tc$^r$ genes on a p15A replication origin. A methylase gene inserted into the Tc$^r$ gene can be expressed constitutively from the Tc promoter.]The transformed cells were plated on L-agar with ampicillin (100 µg/ml) and chloramphenicol (35 µg/ml). Plasmids were isolated from 14 individual colonies from both the genomic DNA and from the pNOTB14.5 derived amplified DNA, using mini plasmid prep procedure as described in step 9. NdeI and SalI double digests of 5µl of each miniprep were compared with NdeI and SalI double digests of pAII17.1 of the 14 genomic derived clones and 2 of the 14 pNOTB14.5 derived clones contained an insert of approximately 1.7 kb. All three of these clones were chosen for further characterization. These 3 clones were grown in 200 ml L-broth with ampicillin and chloramphenicol to a Klett of 80 (mid log phase) and induced with 1 mM IPTG. At 2 hours after induction the cells (approximately 0.8 g) were harvested by centrifugation, washed once in cold Sonication buffer (20 mM Tris-HCl pH 7.5, 1 mM DTT, 0.1 mM EDTA), resuspended in 3 ml of Sonication buffer and sonicated on ice. The sonicated cell extract was centrifuged at 16,000 rpm for 20 minutes. 4.5μl of each extract was mixed with 75μl of a DNA assay mixture (containing 1 μg Adeno2 DNA per 50μl in NEBuffer NotI). 25μl from this tube was mixed with 50μl of the DNA mixture, a 1:2 dilution. 3 other successive 1:2 dilutions were performed. The reactions were incubated at 37° C. for 1 hour. 20μl of the reactions was run on a 1% agarose gel. All 3 clones produced too much NotI restriction endonuclease activity to be titered accurately in this assay; however it was estimated that the enzyme titer was greater than $2.5 \times 10^5$ units/g of cells. Further titrations put the titer of NotI restriction endonuclease activity around $5 \times 10^6$ units/g of cells. This level is about 1,000 times more NotI restriction endonuclease activity per gram of cells than is observed in crude extracts of *Nocardia otitidis-caviarum*. One of these clones was selected for further characterization and was given a strain designation of NEB# 816, with the plasmid named pRM189-1. A sample of NEB# 816 was deposited in accordance with the Budapest Treaty at The American Type Culture Collection at Rockville, Md. on Dec. 3, 1992 accession No. 69139.

12. The NotI restriction endonuclease may be produced from NEB# 816 by propagation to late-log phase in a fermenter containing rich medium with ampicillin (100 μg/ml) and chloramphenicol (35 μg/ml). The culture is then induced by the addition of IPTG to a final concentration of 0.5 mM and allowed to continue growing for 2 hours. The cells are then harvested by centrifugation.

13. Purification of the NotI restriction endonuclease from NEB# 816: All the following procedures were performed either on ice or at 4° C. 18 grams of cells were resuspended in 70 ml of Buffer A (10 mM potassium phosphate pH 6.9, 0.1M NaCl, 0.1 mM EDTA, 5% glycerol) and broken by sonication for 1 minute at full power to an O.D. 260 of 0.13. The extract was centrifuged at 10,000 rpm for 30 min at 4° C. and the resulting supernatant was loaded onto a phosphocellulose column (2.5×15 cm) equilibrated with buffer A. The column was washed with 60 ml buffer A and then a 900 ml linear gradient from 0.1M NaCl to 1.0M NaCl was applied. The restriction enzyme activity eluted at 0.2 to 0.3M NaCl and was pooled. The P-cell pool was dialyzed against buffer B (0.1M NaCl, 10 mM Tris-HCl pH 7.5, 10 mM MgCl$_2$, 5% glycerol and 0.15% NaAzide) overnight and loaded onto a Heparin-Sepharose column (1.5×17 cm) equilibrated with buffer B. The column was washed with 30 ml buffer B, and a 400 ml linear gradient from 0.1M NaCl to 1.2M NaCl was applied. The restriction enzyme activity eluted from the heparin column between 0.5M and 0.6M NaCl and was pooled. The pool was diluted 1:1 with buffer B without NaCl and passed through a DEAE-Sepharose column (1.5×16 cm) equilibrated with buffer B at 0.3M NaCl. The restriction enzyme activity flowed through the column. The flow-through was collected, diluted 1:1 with buffer B no NaCl, and loaded onto a PEI column (1.5×10 cm) equilibrated with buffer B at 0.15M NaCl. The column was washed with 20 ml buffer B, and a 300 ml linear gradient from 0.15M to 1.8M NaCl was applied. The restriction enzyme activity eluted at 0.6M to 0.8M NaCl and was pooled. BSA (bovine serum albumin) was added to the pool to a final concentration of 100 μg/ml. The pool was dialyzed against storage buffer (10 mM Tris-HCl pH 7.5, 0.1 mM EDTA, 0.1M NaCl, 1 mM DTT, 0.15% Triton-X 100 and 50% v/v glycerol). This purification scheme yielded 53,000,000 units of NotI restriction endonuclease.

The NotI restriction endonuclease obtained from this purification was substantially pure and free of non-specific endonuclease and exonuclease. The purity of the NotI restriction endonuclease preparation was checked by looking at the following criteria:

1) Ligation: After a 25-fold overdigestion of Adeno2 DNA, greater than 95% of the DNA fragments produced were ligated with T4 DNA Ligase (at a 5' termini concentration of 1–2 uM at 16° C.). Of these ligated fragments, 95% were able to be recut.
2) Prolonged digestion: After incubating a 50μl reaction containing 1 μg of Adeno2 DNA and 200 units of enzyme for 16 hours, the same pattern of DNA bands was produced as a reaction performed in one hour with one unit of enzyme.
3) Exonuclease Activity: After incubation of 200 units of enzyme for 4 hours at 37° C. in a 50μl reaction containing 1 μg sonicated $^3$H DNA ($10^5$ cpm/μg) less than 0.03% radioactivity was released.
4) Endonuclease Contamination: After incubation of 200 units of enzyme for 4 hours at 37° C. in a 50μl reaction containing 1 μg φX174 RFI DNA, less than 5% was converted to RF II.
5) Megabase genomic Digest: Digestion of one microgram of *E. coli* genomic DNA embedded in 0.5% agarose incubated with 200 u NotI for 16 hours in 100μl NEBuffer#3 resulted in the same limit digest banding pattern as 5 u in 4 hours, as determined by PFG electrophoresis.

All tests were performed in the following reaction buffer:
NEBuffer 3 (100 mM NaCl, 50 mM Tris-HCl, 10 mM MgCl$_2$, 1 mM DTT (pH 7.9 at 25° C.) supplemented with 100 μg/ml BSA.

---

What is claimed is:

1. Isolated DNA coding for NotI restriction endonuclease, wherein the isolated DNA is obtainable from *Nocardia otitidis-caviarum*.

2. A recombinant vector comprising a vector into which DNA coding for NotI restriction endonuclease has been inserted.

3. A recombinant vector comprising the isolated DNA of claim 1.

4. The recombinant vector of claim 3, wherein the vector comprises the plasmid pRM189-1.

5. A host cell transformed with the recombinant vector of claim 2, 3 or 4.

6. A method of producing NotI restriction endonuclease comprising culturing a host cell transformed with the vector of claim 2, 3 or 4 under conditions suitable for expression of said endonuclease.

7. The isolated DNA of claim 1, wherein the isolated DNA comprises SEQ ID NO:17.

* * * * *